United States Patent
Hefer

(10) Patent No.: US 9,724,121 B2
(45) Date of Patent: Aug. 8, 2017

(54) APPARATUS AND METHODS FOR RECANNALIZATION, VALVE REPAIR AND REPLACEMENT

(71) Applicant: Gil Hefer, Shimshit (IL)

(72) Inventor: Gil Hefer, Shimshit (IL)

(73) Assignee: TriReme Medical, LLC, Pleasanton, CA (US)

( * ) Notice: Subject to any disclaimer, the term of this patent is extended or adjusted under 35 U.S.C. 154(b) by 24 days.

(21) Appl. No.: 14/611,996

(22) Filed: Feb. 2, 2015

(65) Prior Publication Data

US 2015/0216552 A1 Aug. 6, 2015

Related U.S. Application Data

(60) Provisional application No. 61/934,778, filed on Feb. 2, 2014.

(51) Int. Cl.
*A61B 17/3207* (2006.01)
*A61M 29/02* (2006.01)
*A61M 25/10* (2013.01)
*A61B 17/22* (2006.01)

(52) U.S. Cl.
CPC ... *A61B 17/320725* (2013.01); *A61M 25/104* (2013.01); *A61M 29/02* (2013.01); *A61B 2017/22061* (2013.01); *A61B 2017/22098* (2013.01); *A61M 2025/109* (2013.01); *A61M 2025/1097* (2013.01)

(58) Field of Classification Search
CPC .. A61B 17/320725; A61B 2017/22098; A61B 2017/320741; A61B 2017/22001; A61B 2017/22051; A61M 2025/1097; A61M 2025/109; A61F 2220/0016; A61F 2/848
See application file for complete search history.

(56) References Cited

U.S. PATENT DOCUMENTS

| | | | |
|---|---|---|---|
| 4,921,984 A | 5/1990 | Nowatari et al. | |
| 4,969,458 A | 11/1990 | Wiktor | |
| 4,998,539 A | 3/1991 | Delsanti | |
| 5,100,423 A | 3/1992 | Fearnot | |
| 5,196,024 A | 3/1993 | Barath | |

(Continued)

FOREIGN PATENT DOCUMENTS

EP  2628455 A1  8/2013

OTHER PUBLICATIONS

International search report and written opinion dated Dec. 7, 2015 for PCT/IB2015/000561.

*Primary Examiner* — Alexander Orkin
(74) *Attorney, Agent, or Firm* — Wilson Sonsini Goodrich & Rosati

(57) ABSTRACT

A scaffold is mounted on a balloon of a balloon catheter. The scaffold has closed cells which deform upon balloon expansion and generate forces that cause struts or other components of the scaffold to deflect outwardly to a diameter that is greater than the inflated diameter balloon. The deflected struts apply forces to fracture plaque of other hardened lesions and also form an annular gap surrounding the balloon to provide for bypass flow of blood or other body fluids. A sheath may be located over the deflected struts to protect adjacent tissue structures from the deflected struts and/or to further define the gap.

14 Claims, 6 Drawing Sheets

(56) References Cited

U.S. PATENT DOCUMENTS

| | | |
|---|---|---|
| 5,221,261 A | 6/1993 | Termin et al. |
| 5,320,634 A | 6/1994 | Vigil et al. |
| 5,397,355 A | 3/1995 | Marin et al. |
| 5,470,314 A | 11/1995 | Walinsky |
| 5,545,132 A | 8/1996 | Fagan et al. |
| 5,591,197 A * | 1/1997 | Orth .................... A61F 2/07 606/191 |
| 5,616,149 A | 4/1997 | Barath |
| 5,624,433 A | 4/1997 | Radisch |
| 5,735,816 A | 4/1998 | Lieber et al. |
| 5,779,698 A | 7/1998 | Clayman et al. |
| 5,797,935 A | 8/1998 | Barath |
| 5,891,090 A | 4/1999 | Thornton |
| 6,123,718 A | 9/2000 | Tu et al. |
| 6,129,706 A | 10/2000 | Janacek |
| 6,190,356 B1 | 2/2001 | Bersin |
| 6,210,392 B1 | 4/2001 | Vigil et al. |
| 6,245,040 B1 | 6/2001 | Inderbitzen et al. |
| 6,355,013 B1 | 3/2002 | Van Muiden |
| 6,394,995 B1 | 5/2002 | Solar et al. |
| 6,425,882 B1 | 7/2002 | Vigil |
| 6,450,988 B1 | 9/2002 | Bradshaw |
| 6,454,775 B1 | 9/2002 | Demarais et al. |
| 7,691,119 B2 | 4/2010 | Farnan |
| 8,080,026 B2 | 12/2011 | Konstantino et al. |
| 8,632,559 B2 | 1/2014 | Gershony et al. |
| 2001/0014822 A1 | 8/2001 | Milo |
| 2002/0002401 A1 | 1/2002 | McGuckin et al. |
| 2002/0007190 A1* | 1/2002 | Wulfman ........ A61B 17/320725 606/167 |
| 2002/0010489 A1* | 1/2002 | Grayzel .................. A61F 2/958 606/194 |
| 2003/0032973 A1 | 2/2003 | Jenusaitis et al. |
| 2003/0153870 A1 | 8/2003 | Meyer et al. |
| 2005/0119678 A1* | 6/2005 | O'Brien ......... A61B 17/320725 606/159 |
| 2005/0288771 A1 | 12/2005 | Majercak et al. |
| 2006/0122684 A1* | 6/2006 | Lye .......................... A61F 2/07 623/1.2 |
| 2007/0093744 A1 | 4/2007 | Elmaleh |
| 2008/0033477 A1 | 2/2008 | Campbell et al. |
| 2009/0105687 A1 | 4/2009 | Deckman et al. |
| 2009/0157159 A1 | 6/2009 | Schneider et al. |
| 2009/0182409 A1 | 7/2009 | Feld et al. |
| 2009/0216314 A1* | 8/2009 | Quadri .................. A61F 2/2418 623/1.17 |
| 2012/0191176 A1 | 7/2012 | Nagl et al. |
| 2013/0218181 A1 | 8/2013 | Feld et al. |
| 2014/0277562 A1* | 9/2014 | Seddon .................. A61F 2/915 623/23.7 |

\* cited by examiner

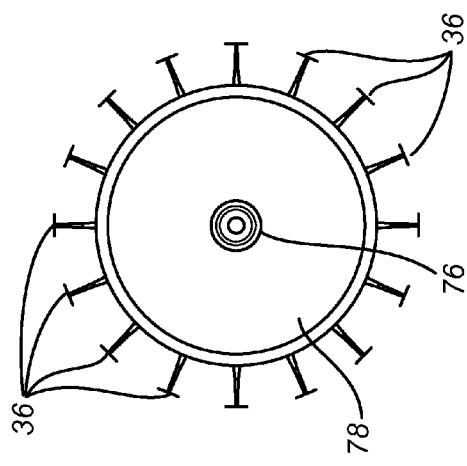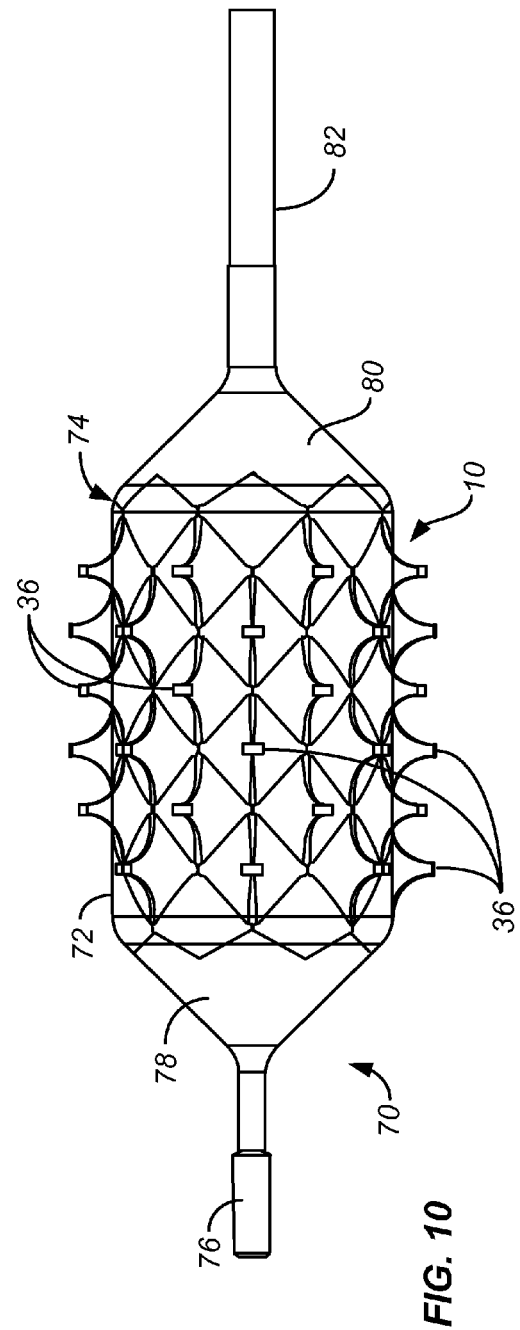

APPARATUS AND METHODS FOR RECANNALIZATION, VALVE REPAIR AND REPLACEMENT

CROSS-REFERENCES TO RELATED APPLICATIONS

This application claims the benefit under 35 USC §119(e) of U.S. Provisional Application No. 61/934,778, filed on Feb. 2, 2014, the full disclosure of which is incorporated herein by reference.

BACKGROUND OF THE INVENTION

1. Field of the Invention

The present invention relates to the field of medical devices and methods, more specifically to devices and methods intended to recannalize body lumens and treat and replace valves in the heart and the vascular system.

Balloon angioplasty is a common medical procedure intended to recannalize stenotic arteries and veins by inserting a balloon catheter through the vascular system. A balloon at the distal end of the catheter is inflated inside a stenosed region in the blood vessel in order to open or "recannalize" the stenosed region and improve blood flow through the vessel.

Aortic valvuloplasty, more commonly referred to as just valvuloplasty, uses a similar balloon inflation protocol to open a stenotic aortic valve, i.e. one that has become stiff and dysfunctional from calcium buildup. The balloon is placed into the aortic valve and inflated in an effort to fracture the calcium build-up and increase the opening size of the valve to improve blood flow from the heart.

Both angioplasty and valvuloplasty suffer from shortcomings. The use of bare balloons for such procedures can require very high inflation pressures which stretch the diseased vessel or valve beyond its elastic limits and which can damage the vessel wall in angioplasty procedures or damage the annulus or tear the valve leaflets in valvuloplasty procedures. Bare balloons can also slip from their intended treatment positions in both angioplasty and valvuloplasty procedures, reducing the effectiveness of the treatments and, in the worst cases, damaging the blood vessel or valve.

To overcome at least some of these problems, the use of balloons carrying cutting blades has been proposed. U.S. Pat. No. 5,320,634 describes the addition of cutting blades to the balloon. The blades can cut the lesions as the balloon is inflated. U.S. Pat. No. 5,616,149 describes a similar method of attaching sharp cutting edges to the balloon. U.S. Patent Publication 2003/0032973 describes a stent-like structure having non-axial grips for securing an angioplasty balloon during inflation. U.S. Pat. No. 6,129,706 describes a balloon catheter having bumps on its outer surface. U.S. Pat. No. 6,394,995 describes a method of reducing the balloon profile to allow crossing of tight lesions. U.S. Patent Publication 2003/0153870 describes a balloon angioplasty catheter having flexible elongate elements that create longitudinal channels in a lesion or stenosis.

As an improvement over balloon catheters having cutting blades, the use of scoring cages and of "quilted" balloons has been proposed. Scoring cage balloons are described in a number of patents and pending application, including U.S. Pat. No. 8,632,559; U.S. Pat. No. 8,080,026: U.S. Pat. No. 7,691,119; and U.S. 2009/0105687. Quilted balloons are described in U.S. 2013/0218181. While highly effective, neither solution is ideal for treating all cases of calcified plaque and other stenotic materials in all patients. In particular, in some instances these cage and balloon designs may not able to generate sufficiently high radial forces to fracture recalcitrant calcified plaque deposits in blood vessels and heart and other valves.

For these reasons, it would be desirable to provide improved or alternative catheters and methods for their use to fracture calcified plaque in blood vessels and valves, particularly in aortic and other heart valves. Moreover, it would be desirable if such balloon structures and methods for their use could provide for improved anchoring of the balloon during dilatation of stenosed vascular regions and valves. Still further, it would be desirable if the balloon and related structures could be adapted for other uses, such as for providing and controlling bypass blood flow, particular in valvuloplasty and prosthetic heart valve replacement procedures and, in some cases, serving as a prosthetic heart valve or a component thereof. At least some of these objectives will be met with the inventions described hereinafter.

2. Description of the Background Art

U.S. Pat. No. 8,632,559; U.S. Pat. No. 8,080,026: U.S. Pat. No. 7,691,119; U.S. Pat. No. 6,394,995; U.S. Pat. No. 6,129,706; U.S. Pat. No. 5,616,149; U.S. Pat. No. 5,320,634; U.S. 2003/0032973; U.S. 2003/0153870; U.S. 20090105687 and U.S. 2013/0218181 have been discussed above. U.S. 2005/0288771 describes a stent for treating bifurcations having a plurality of laterally deployable extensions. U.S. 2009/01822409 describes a stent for treating bifurcations having laterally deployable wings. Other U.S. patents and printed publication of interest include: U.S. Pat. No. 6,454,775; U.S. Pat. No. 6,450,988; U.S. Pat. No. 6,425,882; U.S. Pat. No. 6,355,013; U.S. Pat. No. 6,245,040; U.S. Pat. No. 6,210,392; U.S. Pat. No. 6,190,356; U.S. Pat. No. 6,123,718; U.S. Pat. No. 5,891,090; U.S. Pat. No. 5,797,935; U.S. Pat. No. 5,779,698; U.S. Pat. No. 5,735,816; U.S. Pat. No. 5,624,433; U.S. Pat. No. 5,545,132; U.S. Pat. No. 5,470,314; U.S. Pat. No. 5,221,261; U.S. Pat. No. 5,196,024; U.S. Pat. No. 5,100,423, U.S. Pat. No. 4,998,539; U.S. Pat. No. 4,969,458; and U.S. Pat. No. 4,921,984.

SUMMARY OF THE INVENTION

The present invention provides improved apparatus and methods for recannalizing, including dilatation and fracturing, of calcified and other stenosed regions in the vasculature, heart valves, body lumens, and other tissue regions. These treatments can resize, typically enlarge, the tissue region being treated. Stenosed regions to be treated by the present invention will often include areas of fibrotic, calcified, or otherwise hardened plaque or other stenotic material of the type which can be difficult to dilatate using conventional angioplasty or valvuloplasty balloons. The methods and apparatus of the present will find their greatest use in angioplasty treatment of the arterial vasculature, including but not limited to the coronary arterial vasculature, and in valvuloplasty treatment of aortic and other heart valve stenoses, but may also find use in treatment of the venous and/or peripheral vasculature, treatment of small vessels and/or vessel bifurcations. The methods and apparatus of the present will also find use in providing and controlling bypass blood flow during recanalization procedures as well as during heart valve repair and replacement procedures. Additionally, the apparatus of the present invention can be configured to be implanted as stents, valves, grafts in blood vessel, the heart and other body lumen and tissue regions. When configured for implantation, the scaffolds may be constructed of metals, polymers, and combinations thereof.

In some cases, when constructed in part or entirely from polymers, the polymers may be biodegradable.

In some embodiments of the present invention, a scaffold or other stent-like device is mounted on a balloon of a balloon catheter. When the catheter balloon is deflated, the scaffold contacts or engages an exterior balloon surface. When the catheter balloon is inflated, closed cells or other elements of the scaffold deform and generate forces that cause struts or other components of the scaffold to deflect outwardly and to radially "over expand" to a diameter that is greater than the inflated diameter balloon. When the balloon is inflated, the deflected struts are spaced-above the balloon surface to form a full or partial annular gap between the exterior surface of the balloon and the tops or radially outward tips of the deflected struts. This annular gap can provide for the bypass of blood or other body fluids even when the balloon is fully inflated in a blood vessel or other body lumen. In specific embodiments, a sheath or jacket will be disposed over the deflected struts to further define the gap and/or to protect adjacent tissue structures from the deflected struts.

The present invention can be implemented in various applications and can improve clinical procedures. In some embodiments of the present invention, the scaffold can be implanted devices as a stent with improved positioning and anchoring after implantation as a result of improved anchoring provided by the deflected and over expanded struts. In all cases, the scaffolds may carry or be modified to provide radiopaque markers to assist in the positioning.

In other embodiments of the present invention, the scaffold provides a bypass flow path around the inflated balloon in a blood vessel or tissue opening during a percutaneous transcatheter or other procedure. Once the balloon is expanded, a free space, such as the gap described above, is created between an exterior surface of the expanded balloon and an inner wall of the blood vessel or other tissue opening. The deflected struts or other components act as spacers between the exterior balloon surface and the vessel or other surrounding tissue wall. This creates an annular or other gap that allows bypass blood or other flow. In some cases, a sheath, jacket or other cover may be provided over the deflected struts to further define the bypass flow region. Such sheaths may also be used to protect the surrounding blood vessel or other tissue structures, such as aortic or other valve structures, as described hereinafter. The jacket (sheath) will usually cover at least a cylindrical, central portion of the scaffold body, but optionally could only partially cover the central body portion, for example by being oriented to part face only the aorta or face only the ventricle.

In still other embodiments of the present invention, the scaffold is used to open hardened and calcified lesions in blood vessels, valves, and in other body lumens and tissue structures. The deflecting struts or other components create relatively higher and/or more controlled stress concentrations than cutting blades, cages, and regular stents, in order to fracture hardened vessel calcifications and resize the lumen to a larger diameter.

In further embodiments of the present invention, the scaffold is optionally configured to lock or otherwise be maintained in its deformed state after radial expansion. Thus, the scaffold and the deflected struts can remain in their deployed (expanded) states even following balloon deflation and removal. Such designs allow the scaffold to be implanted as stents, heart valves, heart valve frames, vascular grafts, and the like. In specific configurations, the scaffolds can be designed as a valve frame or as an adaptor between surrounding tissue (valve annulus) and the valve.

In yet other embodiments of the present invention, the scaffold is configured to be temporarily expanded and thereafter returned to its initial state and size, typically being formed from a resilient material and allowed to collapse back to its pre-inflation diameter. Thus, when the balloon is inflated, the scaffold is expanded. When the balloon is deflated, the scaffold collapses back to the initial state. This design is useful for reshaping a tissue without the need for an implant, e.g. angioplasty and valvuloplasty.

In still further embodiments of the present invention, the scaffold is partially or fully covered with a jacket or sheath. The sheath can prevent or inhibit unwanted piercing of tissue by the deflecting struts or other components. Alternatively, the sheath or jacket may be configured to function as a check valve in valvuloplasty procedures to allow blood flow during systole while blocking return flow during diastole. The scaffold and catheter can also be implemented as a temporary valve during the valvuloplasty procedure or, in some designs as a permanently implanted valve prosthesis.

In a first aspect of the present invention, a scaffold comprises a tubular body configured to be carried over a balloon on a balloon catheter. The tubular body includes a plurality of deformable closed cells arranged in axial columns and circumferential rings. Axially adjacent cells are connected to each other at axial connection points, and circumferentially adjacent cells are connected to each other at circumferential connection points. Deformable struts are located within at least some of the closed cells where the struts extend between the axial connection points of that cell. The deformable struts will be configured so that a mid-portion of the strut will deflect radially outwardly as the tubular body is radially expanded which causes the deformable cell to axially shorten. As the axial connection points move axially toward each other, the ends of the deformable struts are collapsed inwardly, forcing their mid-portions to move radially outwardly relative to the tubular body. Usually, the mid-portions of the struts will be initially biased so that they will deform radially outwardly (and not radially inwardly). For example, the struts may be scored on one side to preferentially open outwardly. Alternatively, the mid-portions may be pre-shaped to protrude slightly in the radially outward direction so that radially outward movement is assured.

The deformable struts will usually be distributed uniformly over one or more regions of the tubular body. For example, the struts may be distributed uniformly over one or more circumferential regions of the tubular body, one or more axial regions of the tubular body or some combination of both circumferential regions and axial regions. In the exemplary embodiments, the deformable struts are distributed uniformly over a central region of the tubular body of the scaffold with the proximal and distal end regions being free from any deformable struts. In other embodiments, the deformable struts may be distributed over the entire scaffold region. In yet other embodiments, the struts may be distributed non-uniformly over the tubular body in order to achieve specific purposes, such as anchoring, forming selective gaps with adjacent luminalar tissue structures, or the like.

The closed cells of the tubular scaffold body may generally be any type of deformable closed cell found in conventional stent structures. In the exemplary embodiments, the closed cells are generally rectangular, but they could also be diamond-shaped, formed joining the joining of adjacent pairs of zig-zag stents. In other cases, the closed cells could be formed by joining adjacent serpentine half-rings, or could be formed by patterning a tubular starting material into a variety of specific shapes, such as Palmaz patterns.

The scaffold body may be formed from any conventional balloon-expandable stent or scaffold material, such as stainless steels, cobalt-chromium alloys, tantalum alloys, and in some cases balloon-expandable polymeric materials. In alternative embodiments, the scaffold may be formed from elastic materials which allow the scaffold to be radially constrained to a low profile configuration and then to be released from constraint to assume a radially expanded configuration. The deformable struts will deploy when such self-expanding scaffolds are transition from the constrained configuration to the unconstrained configuration. Examples of useful elastic materials include nickel-titanium alloys, such as Nitinol®, as well as elastic polymers. The stents will usually be formed by laser cutting or otherwise patterning a tubular starting structure into the desired scaffold patterns as described in more detail below.

In specific embodiments, the deformable struts will be configured to engage an adjacent luminal wall or other tissue structure in a desired manner. For example, in the exemplary embodiments, the mid-portion of the deformable strut is provided with a force distribution pad with adjacent legs or segments of the strut extending from the pad to the axial connection points on the deformable cell. An exemplary force distribution pad comprise a rectangular open frame, but other geometries, such as open and closed disks, rings, and the like would also find use. The rectangular frames which are illustrated may be formed to torsionally deflect as the closed cell is axially compressed so that they act as torsion springs to help control deflection of the strut. The struts may have a generally uniform cross-sectional geometry or in other cases may be bifurcated at their ends adjacent to the axial connection points.

In the illustrated embodiments, the open frame of the force distribution pad comprises a first circumferentially oriented beam attached to an inner end of a first segment of the deformable strut and a second circumferentially oriented beam attached to an inner end of a second segment of the deformable strut. The remote ends of each deformable strut segment are attached to the axial attachment points of the deformable cell. Each circumferentially oriented beam torques about its axis as the tubular body is radially expanded by the balloon and the deformable strut deflects radially outwardly.

Optionally, the scaffold may further comprise a sheath or jacket disposed coaxially over at least a portion of the tubular body. The sheath can serve a number of purposes, as generally described above, such as inhibiting or preventing damage to adjacent tissues from the deflected struts, helping to define an annular gap around the scaffold when the balloon is expanded, controlling bypass flow and in particular limiting bypass flow to a single direction, and the like.

In a second aspect of the present invention, assemblies are provided comprising a scaffold as described above in combination with a balloon catheter. The scaffold is disposed over a balloon at or near a distal end of the balloon catheter. The assemblies may further comprise a sheath disposed coaxially over the scaffold, where the sheath is attached to the catheter at locations distal to the balloon and proximal to the balloon. The sheath may have inlet flow ports disposed at a distal end thereof and outlet flow ports disposed at a proximal end thereof. The inlet flow ports are aligned with an annular flow region or gap defined between the balloon and the sheath by the deflected deformable struts when the balloon is inflated or otherwise expanded. The outflow ports are aligned so that they are blocked by the balloon when the balloon is inflated. In this way, when the balloon is inflated, blood may flow in through the inlet ports and into the annular gap surrounding the balloon. The blood will be able to flow outwardly through the outlet ports since the pressure of the blood will cause the sheath to move away from the inflated balloon surface, thus opening a flow path for the blood to exit the annular gap. Conversely, blood flow in the opposite direction will not be able to open the "outflow" ports (since the pressure on the exterior of the sheath will hold the inner surface of the sheath against the distal balloon surface) and the assembly will provide one-way blood flow. This assembly is particularly useful when performing valvuloplasty to allow blood flow from the heart during systole but inhibit blood flow back to the heart during diastole. The structure may also find use as a prosthetic heart valve on a temporary or in some cases permanent basis.

In a third aspect of the present invention, methods for fracturing vascular calcifications, including both luminal calcifications and heart valve calcifications, comprise providing a balloon catheter having a balloon which carries a radially expandable scaffold. The balloon catheter is positioned in a patient's vasculature so that the scaffold is within the vascular calcification. The balloon is then inflated to radially expand the scaffold, where radial expansion of the scaffold deflects a plurality of calcification-engaging elements radially outwardly from the scaffold to engage and fracture the calcification.

Optionally, a sheath may be disposed over the scaffold so that the sheath provides an interface between the calcification-engaging elements and the calcification. Thus, the sheath may inhibit or prevent thethe deflectable struts and other elements of the scaffold from penetrating a blood vessel wall, an adjacent heart valve leaflet or annulus, or other tissue structures.

Still further optionally, the sheath may include flow inlet and outlet ports which are configured to allow blood flow through the sheath. Optionally, the ports may be further configured to provide blood flow in one direction only, such as allowing blood flow during systole and blocking blood flow during diastole when the balloon catheter is being used for valvuloplasty.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 9 is an end view of the scaffold of FIG. 6, where the balloon is inflated and the scaffold is radially expanded to cause the struts to deflect.

FIG. 10 is a side view of the scaffold of FIG. 6, where the balloon is inflated and the scaffold is radially expanded to cause the struts to deflect.

DETAILED DESCRIPTION OF THE INVENTION

Figure 1:
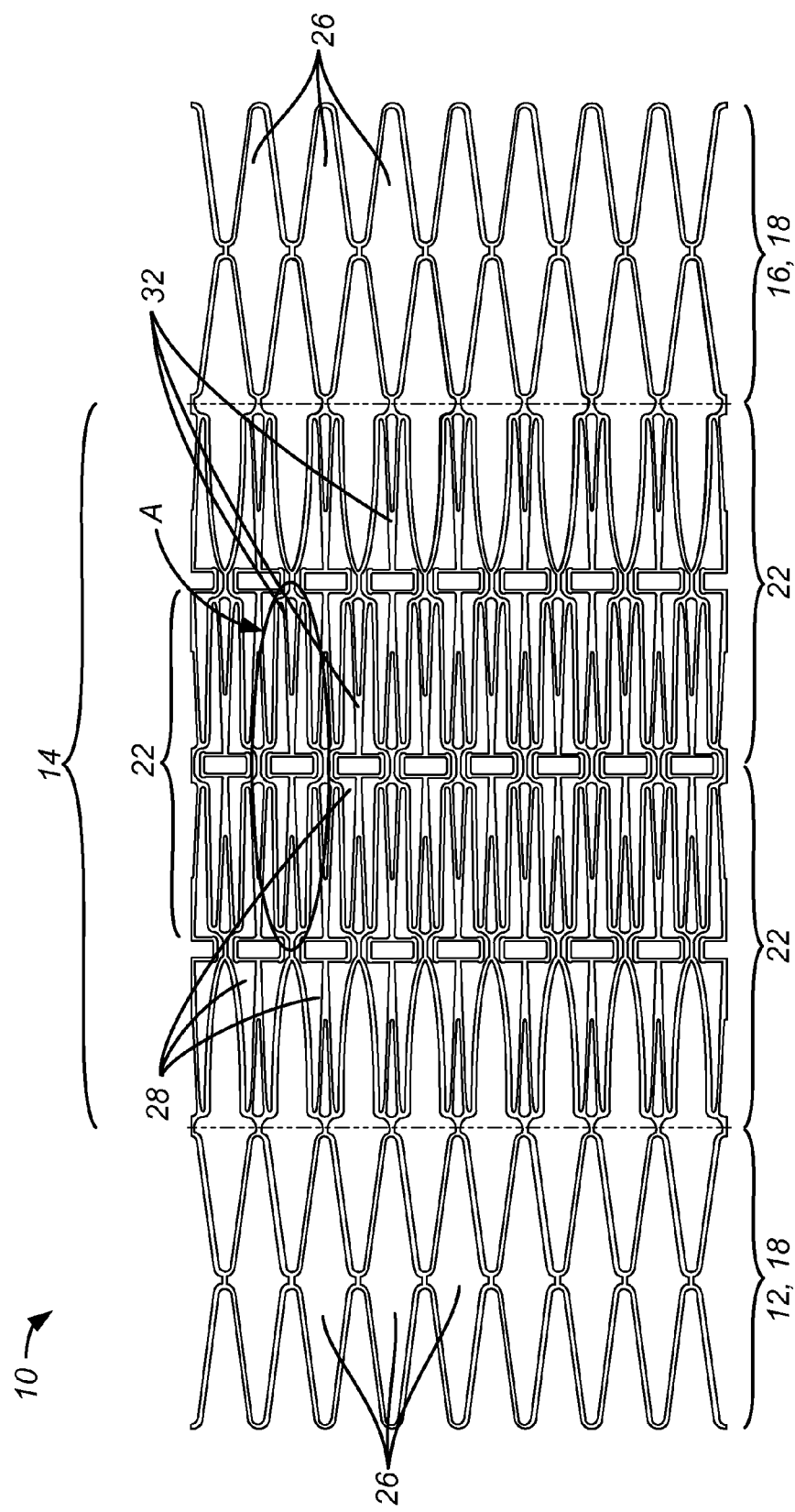
FIG. 1 is a flat or "rolled out" view of an exemplary embodiment of a scaffold having deflecting struts constructed in accordance with the principles of the present invention. The scaffold is shown in its unexpanded state and is divided to three sections A, B, C.

Referring to FIG. 1, a scaffold 10 constructed in accordance with the principles of the present invention is illustrated. The scaffold 10 is shown in a "flattened" view where the cylindrical scaffold body is rolled out into a planar configuration. The scaffold includes a distal section 12, a central section 14, and a proximal section 16. Inclusion of the distal and proximal sections is optional, and these sections if included may have any conventional stent pattern. As shown, distal and proximal sections 12 and 16 comprise rings 18 including opposed zig-zag half-rings that are joined to form generally diamond-shaped closed cells 26. The closed cells are deformable and will axially foreshorten as the scaffold is radially expanded by a balloon, as described in more detail below. Other stent patterns that could be used include serpentine rings, and the like. The central section 14 will also include rings 22 comprising deformable closed cells 28, but the rings and closed cells of the central section will be configured to laterally deploy a plurality of struts 32 as will be described with reference to FIGS. 2-5 below.

Figure 2:
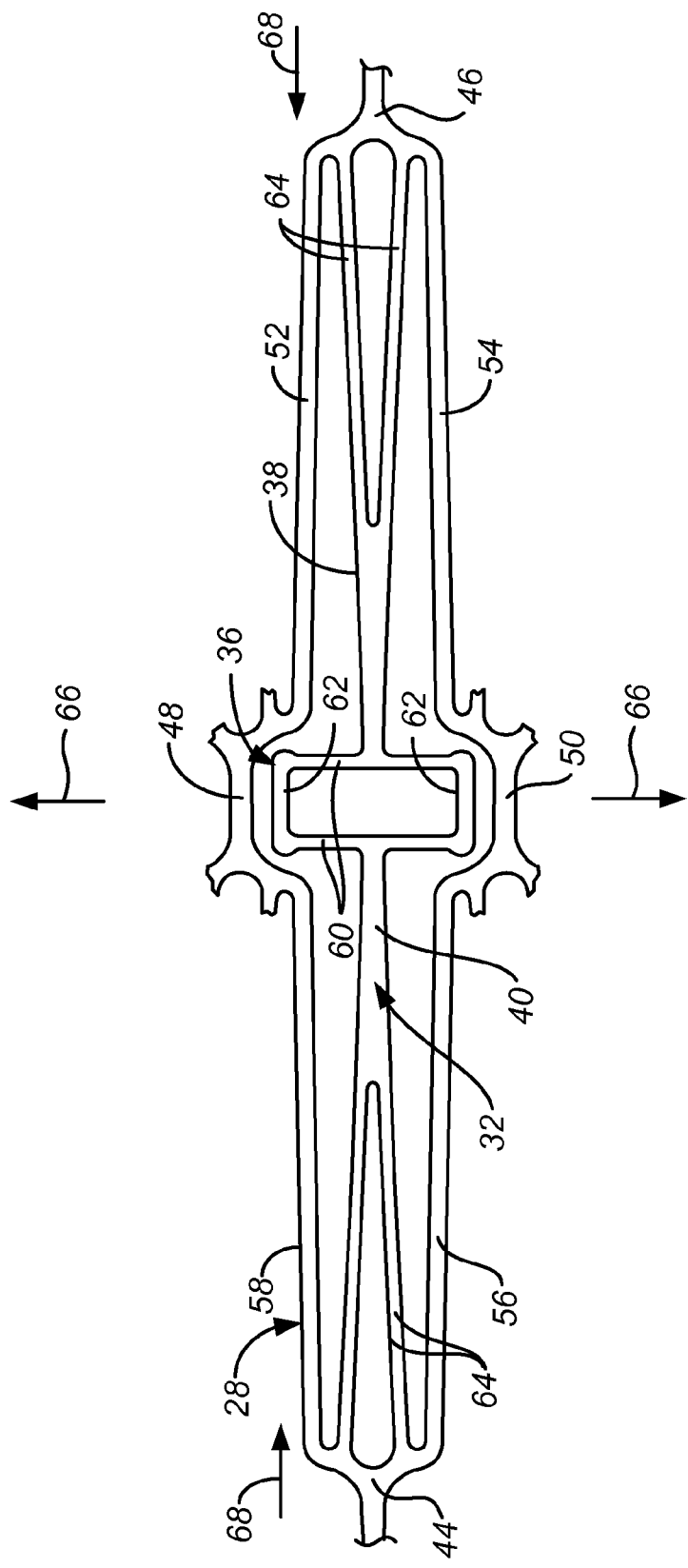
FIG. 2 is a detailed view of one segment or "cell" of section B of the scaffold of FIG. 1 showing a deformable strut in an un-deflected state.
Figure 3:
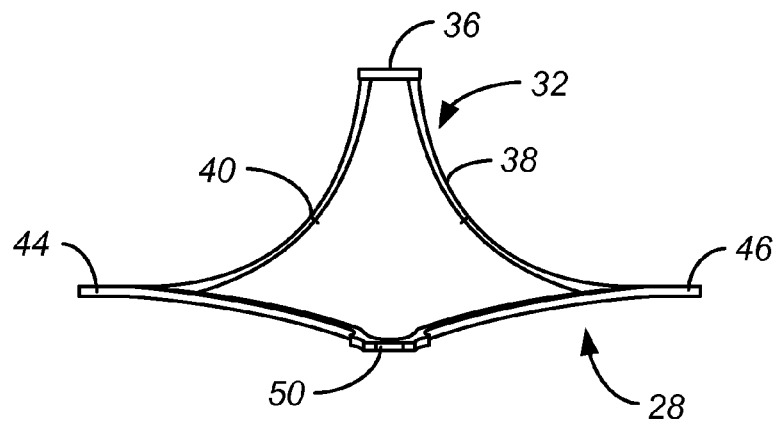
FIG. 3 is a side view of the cell of FIG. 2 shown with the deformable strut in its deflected position.
Figure 4:
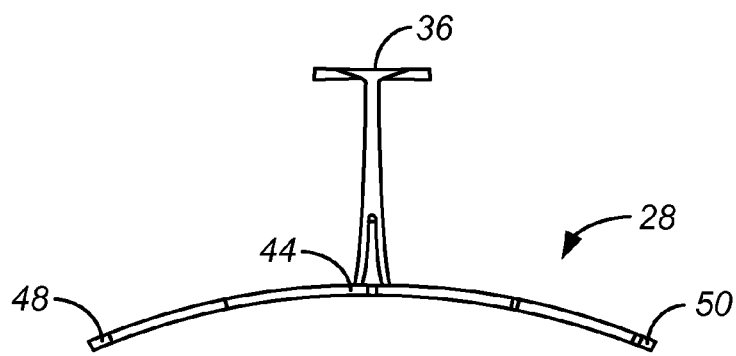
FIG. 4 is a front view of the cell of FIG. 2 shown with the deformable strut in its deflected position.
Figure 5:
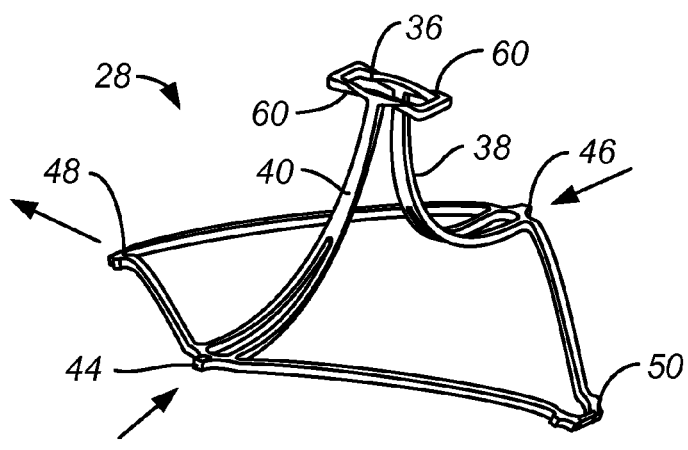
FIG. 5 is an isometric view of the cell of FIG. 2 shown with the deformable strut in its deflected position.

Referring now to FIGS. 2-5, the detailed structure and functioning of the closed cell 28 of scaffold 10 will be described. Each closed cell 28, as best seen in FIG. 2 which is a detailed view of section A of FIG. 1, has a generally rectangular shape with first and second axial attachment points 44 and 46 on axially separated circumferential legs thereof. First and second circumferential attachment points 48 and 50 are provided approximately midway between the first and second axial attachment points on axial legs of each cell. A force distribution pad 36 is supported between first and second segments 38 and 40 of the axial legs of the cells, respectively. The first segment 38 is attached to the second axial attachment point of the cell and the second segment 40 is attached to the first axial attachment point 44. In this way, when the scaffold is radially expanded by an underlying balloon catheter (as illustrated hereinafter), the circumferential attachment points 48 and 50 will be caused to move circumferentially apart (in order to accommodate the increasing diameter of the underlying balloon), as generally shown by arrow 66. Such circumferential separation of the middle of the closed cell 28 will cause the axial attachment points 44 and 46 to move axially inwardly in the direction of arrows 68. Such axial, inward movement, in turn, will axially compress the deformable strut structure 32 causing the mid-portion of the strut, which carries the force distribution pad 36, to move radially outwardly, as illustrated in each of FIGS. 3-5. FIGS. 3-5 show one stage of radial deflection, and it will be appreciated the expansion can be greater or lesser, depending on the degree of radial expansion of the tubular scaffold body by the balloon.

The force distribution pad 36 may have a variety of specific constructions, but as illustrated, includes a pair of circumferential beams 60 joined to a pair of axial beams 62 in a generally rectangular frame pattern. The inner ends of the first and second segments 38 and 40 of the deformable struts 32 are attached to the mid-points of the circumferential beams 60. As best shown in FIG. 5, these circumferential beams 60 may be torqued or twisted as the force distribution pad 36 moves radially outwardly. The circumferential beams 60 thus act as torsion "spring" s to help control lateral deflection of the deformable struts.

In specific embodiments, the first and second segments 38 and 40 of the deformable struts 32 may have bifurcations 64 at each end attached to the axial attachment points.

Figure 6:
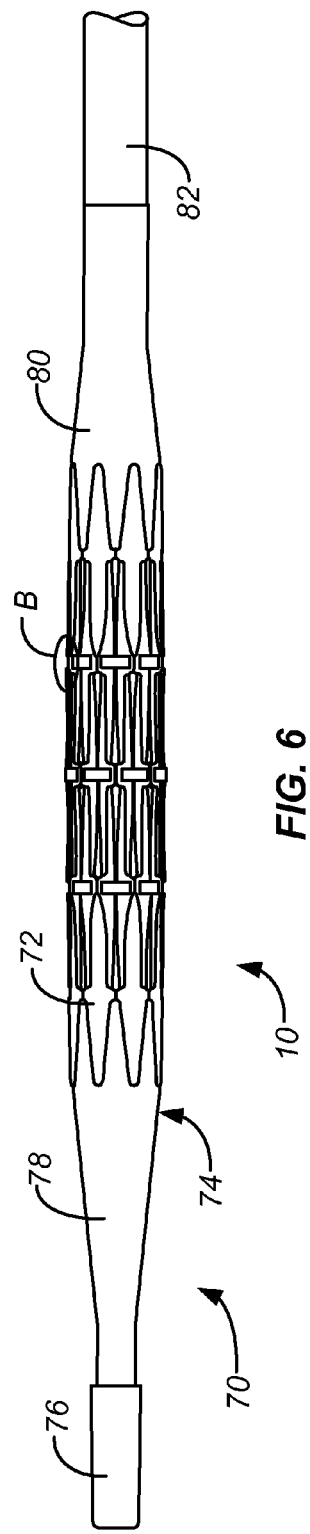
FIG. 6 is a side view of the scaffold of FIG. 1 shown mounted on a catheter balloon in a non-expanded state.
Figure 8:
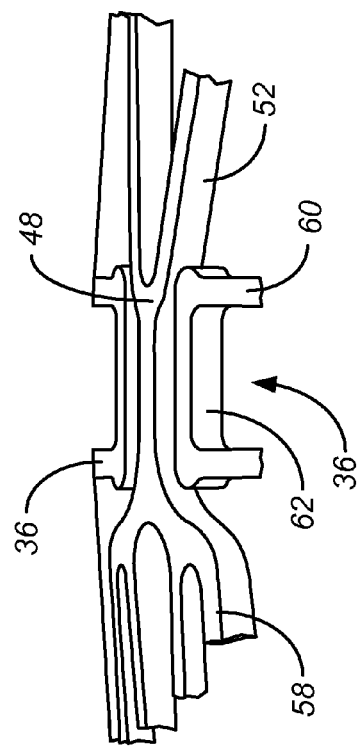
FIG. 8 is an enlarged, detailed view of region B of FIG. 6.
Figure 7:
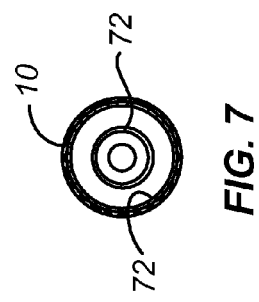
FIG. 7 is an end view of the scaffold of FIG. 6 mounted on a catheter balloon.

Referring now to FIGS. 6-8, the scaffold 10 may be mounted on a balloon catheter 70. In particular, scaffold 10 may be placed over a working or cylindrical area 72 of the balloon of the balloon catheter prior to inflation. The catheter will typically include distal tip 76, a distal cone 78, a proximal cone 80, and a shaft 82.

As shown in FIG. 8, the center portions of the deformable struts 32 which carry the force distribution pads 36 may be pre-shaped and/or biased so that the center portions are slightly bent in a radially outward direction so that, upon axial compression of the deformable struts 32, the center portions including the force distribution pads 36 will move radially outwardly and avoid any tendency to move radially inwardly.

Referring now to FIGS. 9 and 10, after the balloon 74 of the balloon catheter 70 is inflated, the force distribution pads 36 of the scaffold 10 will be raised radially above the balloon surface creating a potential gap between the upper ends or tips of the deflected struts (which carry the force distribution pads 36) and the exterior surface of the balloon.

Figure 12:
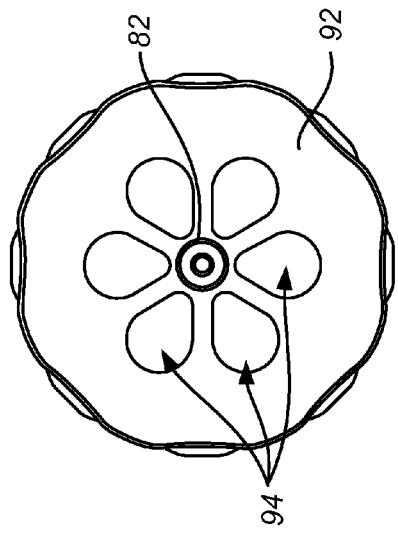
FIG. 12 is a proximal end view of the scaffold of FIG. 6, where the balloon is inflated and the scaffold is radially expanded to cause the struts to deflect. The scaffold is covered with a sheath or jacket which includes holes (outlet ports) configures to allow bypass blood flow during valvuloplasty or other procedures.
Figure 13:
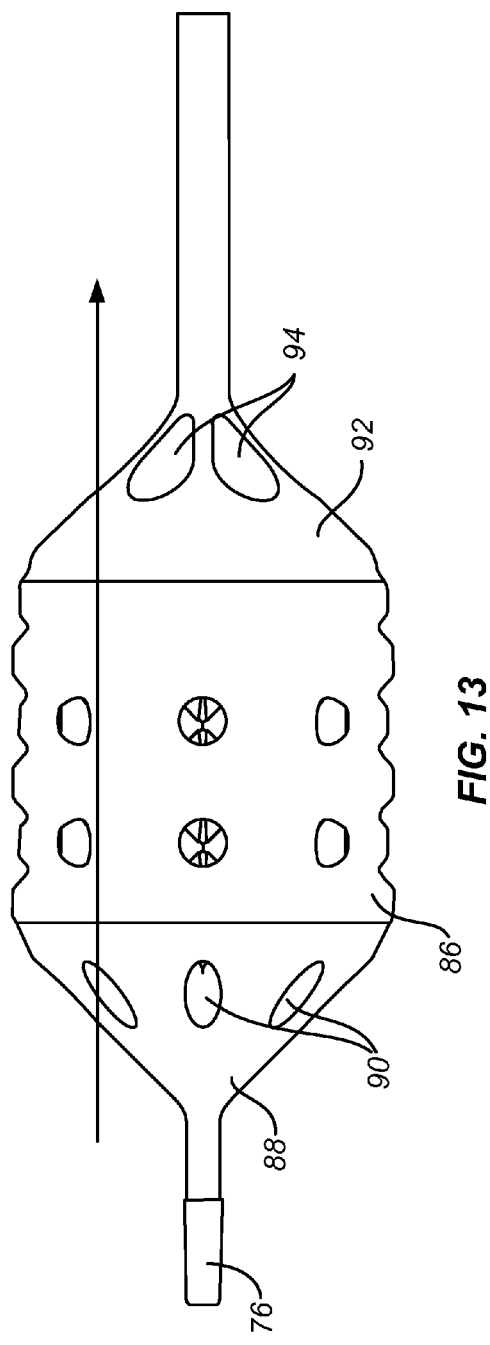
FIG. 13 is a side view of the scaffold of FIG. 6, where the balloon is inflated and the scaffold is radially expanded to cause the struts to deflect. The scaffold is covered with a sheath or jacket which includes holes configured to allow bypass blood flow during valvuloplasty or other procedures.
Figure 11:
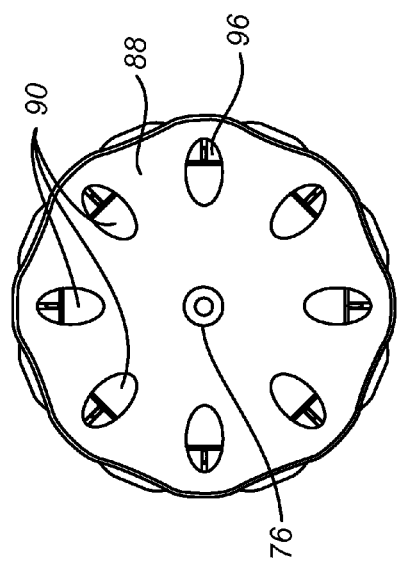
FIG. 11 is a distal end view of the scaffold of FIG. 6, where the balloon is inflated and the scaffold is radially expanded to cause the struts to deflect. The scaffold is covered with a sheath or jacket which includes holes (inlet ports) configured to allow bypass blood flow during valvuloplasty or other procedures.

As shown in FIGS. 11-13, the deployed or laterally deflected landing pads 36 may be used to open and support a jacket or sheath 86 which is initially placed around the scaffold prior to deployment of the deflectable struts. The sheath 86 may serve to protect luminal walls and valve structures from damage when the scaffold is expanded therein, particularly from the struts 32 as they are deflected radially outwardly. Additionally, the sheath 86 may help further define the annular gap between the tops of the deflected struts 32 and the balloon surface. In such cases, a distal surface 88 of the sheath may have distal or inlet ports 90 formed therein, and a proximal surface 92 of the sheath may have proximal or outlet ports 94 formed therein. The distal inlet ports 90 will typically be aligned with the annular gap 96 formed between the exterior of the balloon and the interior of the sheath. In this way, blood or other body fluids may flow into the gap through the inlet port 90 as the path is clear. The blood may also flow outwardly in the direction of the arrow through the outlet ports 94. While these outlet ports 94 will typically be positioned over the proximal cone 80 of the balloon when inflated, the blood or other fluid pressure will separate the sheath from the balloon, allowing outflow of the blood or other fluid. Conversely, if the flow were in the other direction (in a direction opposite to the illustrated arrow), the blood would be prevented from entering the annular gap by the presence of the proximal cone 80 of the balloon blocking the proximal ports 94. Thus, the scaffold of the present invention, when used in combination with a sheath and balloon catheter, may form a one-way flow structure. The one-way flow structure will be useful when the device is used for valvuloplasty. Also, if the device is configured to be implantable, the structure could serve as a functioning prosthetic heart or other luminal valve.

It will be appreciated by persons skilled in the art that the present invention is not limited to what has been particularly shown and described hereinabove. Alternate embodiments are contemplated that fall within the scope of the invention.

What is claimed is:

1. A scaffold comprising:
   a tubular body configured to be carried over a balloon on a balloon catheter, said body including a plurality of deformable closed cells arranged in axial columns and circumferential rings, wherein axially adjacent cells are connected at axial connection points and circumferentially adjacent cells are connected at circumferential connection points; and
   deformable struts extending between the axial connection points within at least some of the deformable cells, wherein each strut includes a first segment and a second segment which meet at configured so that a mid-portion of the strut deflects radially outwardly as the cell axially shortens as the tubular body is radially expanded by the balloon, wherein the mid-portion is biased to open radially outwardly as the strut is axially compressed by the axial shortening of the cell, wherein the mid-portion of the strut includes a force distribution pad comprising an open frame having a first circumferentially oriented beam attached to an inner end of the first segment of the deformable strut and a second circumferentially oriented beam attached to an inner end of the second segment of the deformable strut, wherein remote ends of each deformable strut segment are attached to the axial attachment points of the cell, and wherein each circumferentially oriented beam torques about its axis as the tubular body is radially expanded by the balloon and the deformable strut deflects radially outwardly.

2. A scaffold as in claim 1, wherein the deformable struts are distributed uniformly over one or more circumferential regions of the tubular body.

3. A scaffold as in claim 1, wherein the deformable struts are distributed uniformly over one or more axial regions of the tubular body.

4. A scaffold as in claim 1, wherein the deformable struts are distributed uniformly over the entire tubular body.

5. A scaffold as in claim 1, wherein the cells in one or more circumferential regions of the tubular body do not have the deformable struts therein.

6. A scaffold as in claim 1, wherein the cells in a first circumferential region of a first end of the tubular body and in a second circumferential region of a second end of the tubular body do not have the deformable struts therein.

7. A scaffold as in claim 1, wherein the cells are diamond-shaped.

8. A scaffold as in claim 1, wherein the cells are defined by adjacent separate rings.

9. A scaffold as in claim 1, wherein the cells are defined by adjacent zig-zag rings.

10. A scaffold as in claim 1, wherein the open frame is rectangular or circular.

11. A scaffold as in claim 1, wherein the ends of each segment of the deformable strut which are attached to the axial connection points are bifurcated.

12. A scaffold as in claim 1, further comprising a sheath disposed coaxially over at least a portion of the tubular body.

13. An assembly comprising:
    a scaffold as in claim 1; and
    a balloon catheter having proximal and distal ends and a balloon disposed near the distal end thereof, wherein the scaffold is disposed over the balloon.

14. An assembly as in claim 13, further comprising a sheath disposed coaxially over the scaffold and attached to the catheter at locations distal to the balloon and proximal to the balloon.

* * * * *